United States Patent
Zhong et al.

(10) Patent No.: US 10,399,992 B2
(45) Date of Patent: Sep. 3, 2019

(54) PROCESS FOR PREPARING AD-35

(71) Applicant: Zhejiang Hisun Pharmaceutical Co., Ltd., Taizhou (CN)

(72) Inventors: Jinqing Zhong, Taizhou (CN); Xuyang Zhao, Chengdu (CN); Hua Bai, Taizhou (CN); Yongxiang Gong, Taizhou (CN); Xinlong Zhang, Taizhou (CN); Qifeng Zhu, Taizhou (CN); Weiwei Liu, Taizhou (CN); Ya Zhou, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 0 days.

(21) Appl. No.: 16/087,308

(22) PCT Filed: Mar. 28, 2017

(86) PCT No.: PCT/CN2017/078389
§ 371 (c)(1),
(2) Date: Sep. 21, 2018

(87) PCT Pub. No.: WO2017/177816
PCT Pub. Date: Oct. 19, 2017

(65) Prior Publication Data
US 2019/0100527 A1  Apr. 4, 2019

(30) Foreign Application Priority Data
Apr. 11, 2016 (CN) .......................... 2016 1 0221284

(51) Int. Cl.
C07D 491/056 (2006.01)
C07D 491/113 (2006.01)
A61P 25/28 (2006.01)

(52) U.S. Cl.
CPC ...... C07D 491/056 (2013.01); C07D 491/113 (2013.01); *A61P 25/28* (2018.01); *Y02P 20/55* (2015.11)

(58) Field of Classification Search
CPC .............................. C07D 491/056; A61P 25/28
USPC ........................................................ 548/430
See application file for complete search history.

(56) References Cited

U.S. PATENT DOCUMENTS

| 2008/0153878 A1 | 6/2008 | Bhat et al. |
| 2009/0137629 A1 | 5/2009 | Iimura et al. |
| 2015/0191480 A1 | 7/2015 | Bai et al. |

FOREIGN PATENT DOCUMENTS

| CN | 101626688 A | 1/2010 |
| CN | 103524515 A | 1/2014 |
| CN | 105859732 A | 8/2016 |
| WO | 2014005421 A1 | 1/2014 |

OTHER PUBLICATIONS

Chinese Search Report for Application No. 2016102212846, dated Aug. 2, 2017.
Gong, et al., "Design, Synthesis and Biological Evaluation of Novel [1,3] Dioxolo [4,5-f] Isoindolone Derivatives", Acta Pharmaceutica Sinica, vol. 50, No. 2, Feb. 2015, pp. 191-198.
International Search Report for Application No. PCT/CN2017/078389, dated Jul. 5, 2017.
Kleppinger, et al., "Discotic Liquid Crystals Through Molecular Self-Assembly", Journal of the American Chemical Society, vol. 119, No. 18, May 1997, pp. 4097-4102.
Sarell, et al., "Substoichiometric Levels of Cu2+ Ions Accelerate the Kinetics of Fiber Formation and Promote Cell Toxicity of Amyloid-B from Alzheimer Disease", Journal of Biological Chemistry, Oct. 2010, pp. 41533-41540.
Taiwanese Search Report for Application No. 106112069, dated Feb. 7, 2018.

*Primary Examiner* — Kristin A Vajda
(74) *Attorney, Agent, or Firm* — Lerner, David, Littenberg, Krumholz & Mentlik, LLP

(57) ABSTRACT

Disclosed are a method for preparing a benzodioxole derivative (AD-35) shown by Formula (I) and an intermediate thereof. The method of the present invention involves: using piperic acid as a raw material; and performing bromination, esterification, cyanidation, cyclopropane lactamization, amide nitrogen alkylation, deprotection, piperidine nitrogen alkylation and salification to obtain the compound of Formula (I). The method has cheap and easily available start raw materials, short synthesis routes and simple operation, and is suitable for industrial production.

I

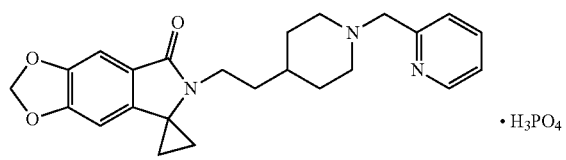

· $H_3PO_4$

26 Claims, No Drawings

PROCESS FOR PREPARING AD-35

CROSS REFERENCE TO RELATED APPLICATIONS

The present application is a national phase entry under 35 U.S.C. § 371 of International Application No. PCT/CN2017/078389, filed Mar. 28, 2017, which claims priority from Chinese Patent Application No. 201610221284.6 filed Apr. 11, 2016, all of which are hereby incorporated herein by reference.

TECHNICAL FIELD

The present application relates to a method for preparing a clinical trial drug shown by Formula (I) for treating Alzheimer's disease, i.e. 6-[2-[1-(2-pyridylmethyl)-4-piperidinyl]ethyl]spiro[[1,3]dioxolo[4,5-f]isoindole-7,1'-cyclopropane]-5-one phosphate (AD-35), and synthetic intermediates thereof.

BACKGROUND OF ART

WO2014005421 reports a class of benzodioxole compounds, which have an activity of inhibiting acetylcholinesterase and can be used for treating Alzheimer's disease. Of particular interest in this class of compounds is 6-[2-[1-(2-pyridylmethyl)-4-piperidinyl]ethyl]spiro[[1,3]dioxolo[4,5-f]isoindole-7,1'-cyclopropane]-5-one phosphate, with a code of AD-35, chemical structure thereof is shown in Formula I below:

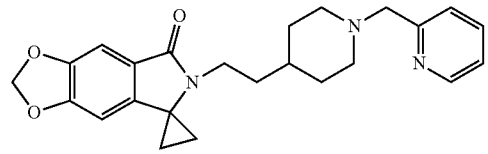

I · H$_3$PO$_4$

AD-35 is a relatively weak acetylcholinesterase inhibitor, the activity of inhibiting acetylcholinesterase in vitro of AD-35 is about one-tenth of the activity of donepezil. However, this compound shows comparable efficacy to that of donepezil in the Morris water maze test, that is, the effect of improving memory and learning ability thereof is comparable to that of donepezil. This shows that AD-35 is likely to produce effects of improving memory and learning ability through other mechanisms in vivo. Further studies using a rat model of Alzheimer's disease induced by Aβ$_{25-35}$ found that AD-35 can significantly inhibit the production and release of the pro-inflammatory cytokines TNF-α and IL-1β, thereby greatly reduces the toxicity of Aβ$_{25-35}$ to nerve cells, and protects nerve cells effectively.

In addition, AD-35 also exhibits a certain ability to chelate transition metal ions such as Cu$^{2+}$ in vitro, while Cu$^{2+}$ can accelerate the formation of Aβ fibers and enhance the toxicity of Aβ to nerve cells, thereby promotes the death of nerve cells. Therefore, excessive Cu$^{2+}$ in brain is also believed to be one of the risk factors for Alzheimer's disease (Sarell et al. J. Biol. Chem. 2010, 285(53), 41533). In view of chemical structure, two nitrogen atoms respectively in the piperidine ring and pyridine ring in AD-35 molecule constitute a structural unit similar to ethylenediamine, which could explain why this compound can chelate transition metal ions to some extent. In terms of safety of a compound, acute toxicity test in mice shows that AD-35 is much less toxic than donepezil. The recent Phase 1 Clinical Single Ascending Dose study (SAD) indicated that subjects did not develop adverse reactions by taking 90 mg of AD-35 in a single dose, which indicates that the compound has a favorable safety.

In summary, AD-35 is promising to be a new drug for treating Alzheimer's disease with minor side effects. Its multiple mechanism of action is likely to make this compound not only alleviate the symptoms of Alzheimer's patients, but also delay the progression of this disease.

Since the synthesis route for preparing AD-35 and analogs thereof reported in WO2014005421 is too long, the operation is complicated, the yield is low, and some steps are not applicable to industrial production, it is necessary to develop a new process route to overcome the existing problems of the preparation method above.

SUMMARY OF THE INVENTION

In order to solve the above technical problems, one of the objects of the present application is to provide a key intermediate (the compound of Formula V) for preparing a compound of Formula (I) and a preparation method thereof:

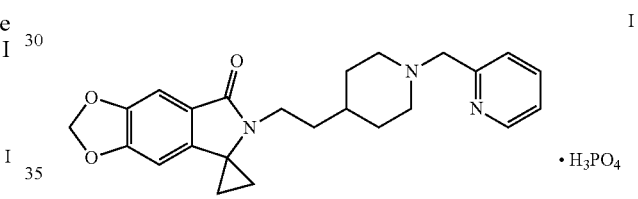

I · H$_3$PO$_4$

In a first aspect of the application, provided is an intermediate shown by Formula V which can be used to prepare a compound of Formula (I):

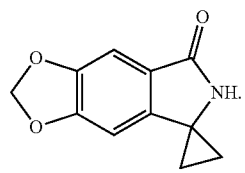

V

In another aspect of the present application, provided is a method for preparing a compound represented by Formula V, the method comprises: performing a cyclopropane lactamization of a cyano ester shown by Formula IV under the action of titanium (IV) isopropoxide (Ti(Oi-Pr)$_4$) and a Grignard reagent of ethylmagnesium halide to obtain a spirocyclopropane lactam shown by Formula V:

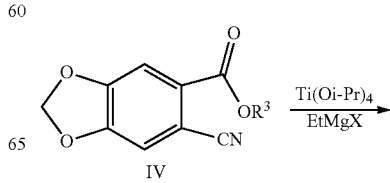

IV

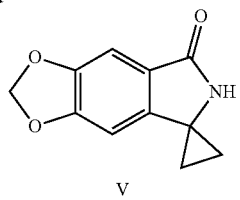

wherein $R^3$ is $C_1$-$C_6$ alkyl; X is chlorine, bromine or iodine.

The Grignard reagent of ethylmagnesium halide of this reaction is preferably ethylmagnesium bromide.

The solvent of this reaction is selected from the group consisting of diethyl ether, dichloromethane, toluene, methyl tert-butyl ether or tetrahydrofuran, preferably dichloromethane.

The temperature of the reaction is controlled to be 0 to 35° C., preferably 0 to 20° C.

In this reaction, the molar ratio of the compound shown by Formula IV to titanium (IV) isopropoxide (Ti(Oi-Pr)$_4$) is 1:1 to 1:3, preferably 1:1 to 1:1.5.

In this reaction, the molar ratio of the compound shown by Formula IV to the Grignard reagent of ethylmagnesium halide is 1:1 to 1:5, preferably 1:2 to 1:3.

In still another aspect of the present application, provided is a method for preparing a compound represented by Formula VII, the method comprises: coupling a spirocyclopropane lactam shown by Formula V with a compound shown by Formula VI under the action of a base to obtain the compound shown by Formula VII:

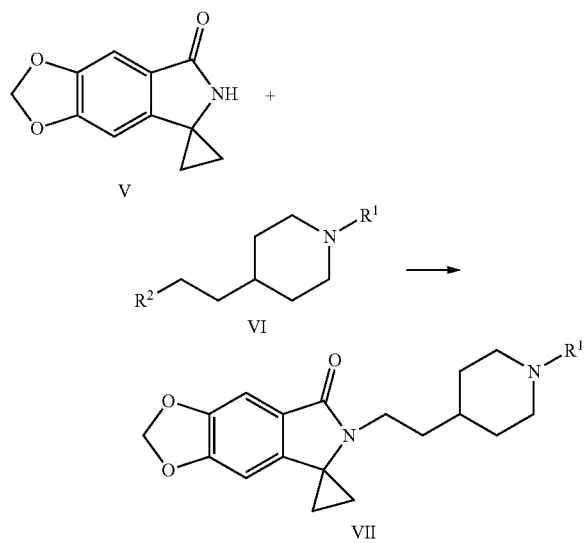

wherein $R^1$ is a protecting group of amino, preferably tert-butoxycarbonyl (Boc); $R^2$ is halogen or p-toluenesulfonyloxy.

The base used in this reaction is selected from the group consisting of sodium hydride, potassium tert-butoxide, sodium hydroxide, potassium hydroxide or cesium carbonate, preferably sodium hydroxide or potassium hydroxide.

In this reaction, the molar ratio of the compound shown by Formula V to the base is 1:1 to 1:3, preferably 1:1.1 to 1:2.

In this reaction, the molar ratio of the compound shown by Formula V to the compound shown by Formula VI is from 1:1 to 1:3, preferably from 1:1.1 to 1:1.5.

The solvent for this reaction is selected from the group consisting of N,N-dimethylformamide, dimethyl sulphoxide or acetonitrile, preferably dimethyl sulphoxide.

The temperature of this reaction is controlled to be 25 to 75° C., preferably 55 to 65° C.

Another object of the present application is to provide a method for preparing a compound of Formula (I) based on above intermediate, thereby to provide an improved simple method to prepare a benzodioxole derivative of Formula (I) which can inhibit acetylcholinesterase with a high yield. That is, the method for preparing the compound of 6-[2-[1-(2-pyridylmethyl)-4-piperidinyl]ethyl]spiro[[1,3]dioxolo[4,5-f]isoindole-7,1'-cyclopropane]-5-one phosphate.

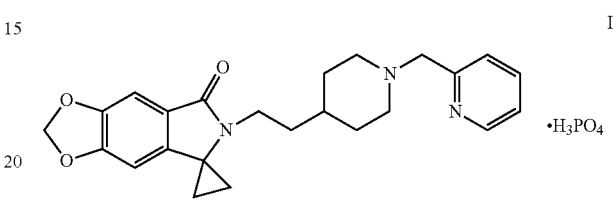

The method comprises the following steps:

(1) In the solvent, salifying piperic acid under the action of a base and following with a bromination under the action of N-bromosuccinimide (NBS) to obtain a compound shown by Formula II:

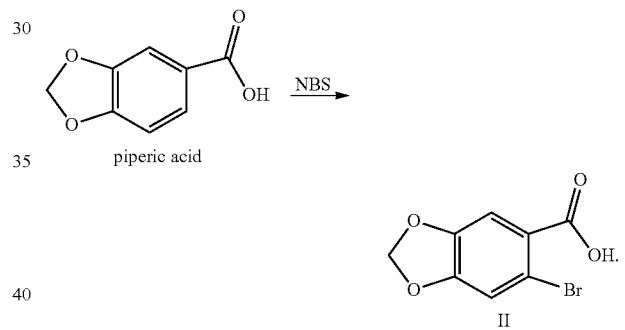

(2) Performing an esterification reaction of the compound shown by Formula II with an alcohol (R$^3$OH) under the catalysis of an acid to obtain an ester shown by Formula III:

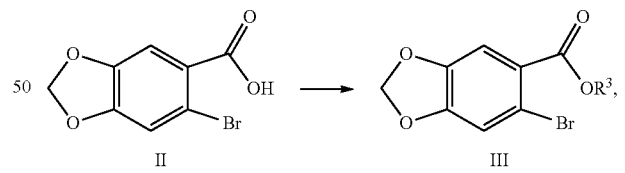

wherein $R^3$ is $C_1$-$C_6$ alkyl.

(3) Cyaniding the compound shown by Formula III under the action of a cyanide ion donor to obtain a cyano ester shown by Formula IV:

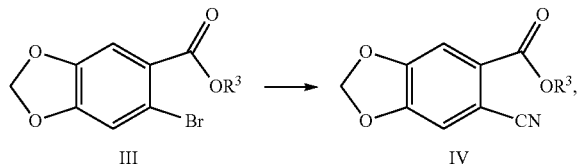

wherein $R^3$ is $C_1$-$C_6$ alkyl.

(4) Performing a cyclopropane lactamization of the cyano ester shown by Formula IV under the action of titanium (IV) isopropoxide (Ti(Oi-Pr)$_4$) and a Grignard reagent of ethylmagnesium halide to obtain a spirocyclopropane lactam shown by Formula V:

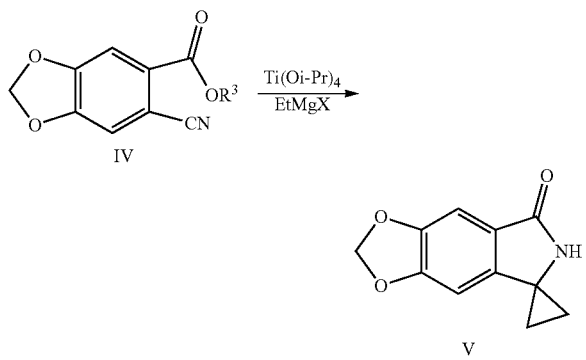

wherein R$^3$ is C$_1$-C$_6$ alkyl; X is chlorine, bromine or iodine.

(5) Coupling the spirocyclopropane lactam shown by Formula V with the compound shown by Formula VI under the action of a base to obtain a compound shown by the Formula VII:

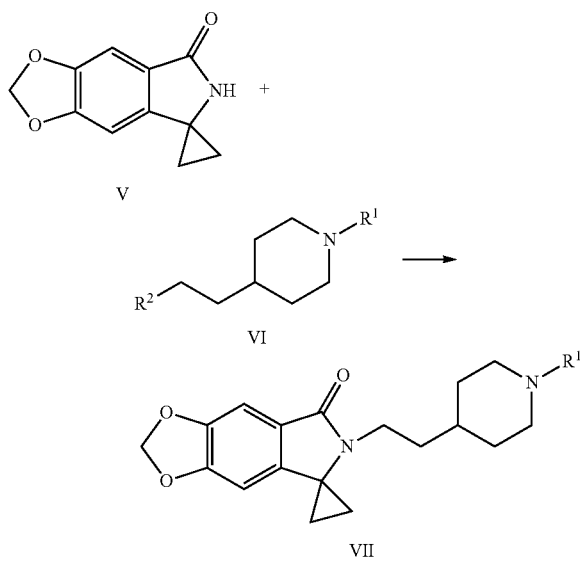

wherein R$^1$ is a protecting group of amino, preferably tert-butyloxycarbonyl (Boc); R$^2$ is halogen or p-toluenesulfonyloxy.

(6) Removing the protecting group of amino of the compound shown by Formula VII to obtain a compound shown by Formula VIII or a salt thereof:

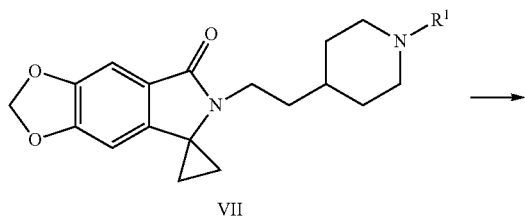

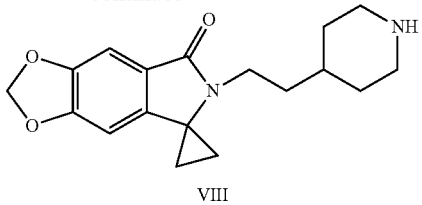

wherein R$^1$ is an protecting group of amino, preferably tert-butyloxycarbonyl (Boc).

(7) Reacting the compound shown by Formula VIII or a salt thereof with a compound shown by Formula IX or a salt thereof under the action of a base to obtain a compound shown by Formula XI:

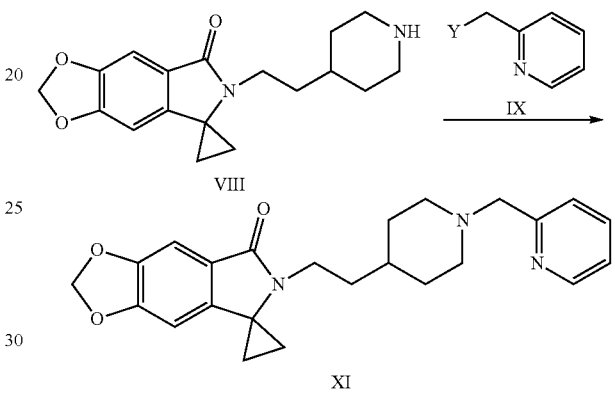

wherein Y is halogen or sulfonyloxy.

(8) Salifying the compound shown by Formula XI with phosphoric acid to obtain the compound of Formula I:

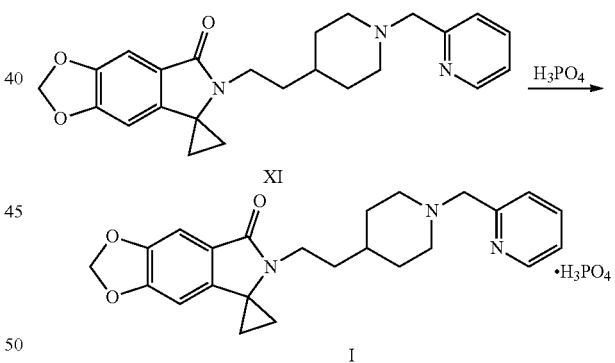

In the above reaction steps, wherein,

In step (1), the reaction solvent is selected from the group consisting of N,N-dimethylformamide, N,N-dimethylacetamide, water, dichloromethane or chloroform, preferably water; the base is selected from the group consisting of sodium hydroxide, potassium hydroxide, sodium hydrogencarbonate, sodium carbonate or potassium carbonate; the molar ratio of the piperic acid, base and N-bromosuccinimide (NBS) is 1:1.2-2:1.4-2.4; the reaction temperature is controlled to be 0 to 70° C., preferably 30 to 45° C.

In step (2), R$^3$ is a C$_1$-C$_6$ alkyl, preferably a methyl, an ethyl or an isopropyl, more preferably an ethyl; this reaction is known in the art, that is, the compound shown by Formula II is esterified with an alcohol (R$^3$OH) under the catalysis of an acid, wherein the acid used for catalysis is preferably concentrated sulfuric acid.

In Step (3), the cyanide ion donor is a metal cyanide, preferably a cuprous cyanide (CuCN) or potassium ferrocyanide/copper iodide ($K_4Fe(CN)_6$/CuI), more preferably potassium ferrocyanide/cuprous iodide ($K_4Fe(CN)_6$/CuI);

More preferably, the molar ratio of the compound shown by Formula III to cuprous iodide (CuI) is 1:1 to 1:2, preferably 1:1.1 to 1:1.5; the molar ratio of the compound shown by Formula III to potassium ferrocyanide ($K_4Fe(CN)_6$) is 1:0.15 to 1:0.35, preferably 1:0.18 to 1:0.25, the reaction temperature is controlled to be 100 to 160° C., preferably 120 to 140° C.; the reaction solvent is preferably N,N-dimethylformamide or N,N-dimethylacetamide.

In step (4), the Grignard reagent of ethylmagnesium halide is preferably an ethylmagnesium bromide, the solvent is selected from the group consisting of diethyl ether, dichloromethane, toluene, methyl tert-butyl ether or tetrahydrofuran, preferably dichloromethane; the reaction temperature is controlled to be 0 to 35° C., preferably 0 to 20° C.; the molar ratio of the compound shown by Formula IV to titanium (IV) isopropoxide ($Ti(Oi-Pr)_4$) is 1:1 to 1:3, preferably 1:1 to 1:1.5; the molar ratio of the compound shown by Formula IV to the Grignard reagent of ethylmagnesium halide is 1:1 to 1:5, preferably 1:2 to 1:3.

In step (5), $R^1$ is a protecting group of amino, preferably tert-butyloxycarbonyl (Boc); $R^2$ is halogen or p-toluenesulfonyloxy; the base used in the reaction is selected from the group consisting of sodium hydride, potassium tert-butoxide, sodium hydroxide, potassium hydroxide or cesium carbonate, preferably sodium hydroxide or potassium hydroxide; the molar ratio of the compound shown by Formula V to the base is 1:1 to 1:3, preferably 1:1.1 to 1:2; the molar ratio of the compound shown by V to the compound shown by VI is 1:1 to 1:3, preferably 1:1.1 to 1:1.5; the reaction solvent is selected from the group consisting of N,N-dimethylformamide, dimethyl sulfoxide or acetonitrile, preferably dimethyl sulfoxide; the reaction temperature is controlled to be 25 to 75° C., preferably 55 to 65° C.

In the step (6), when $R^1$ is tert-butoxycarbonyl, and when removing the protecting group of amino under an acidic condition, the acid is selected from the group consisting of sulfuric acid, trifluoroacetic acid, hydrofluoric acid or hydrochloric acid, preferably hydrochloric acid (the hydrochloric acid used in this reaction is not particularly limited, anyone in the concentrated hydrochloric acid, hydrogen chloride gas, hydrogen chloride gas-absorbed solvent, solvent-diluted mixed liquid of concentrated hydrochloric acid may be used); the reaction solvent used is selected from the group consisting of methanol, ethanol, ethyl acetate or a mixed solvent thereof, preferably a mixed solvent of ethanol and ethyl acetate, more preferably a volume ratio of ethanol to ethyl acetate is 2:3; the reaction temperature is controlled to be 20 to 70° C., preferably 50 to 60° C.

In step (7), Y in the compound shown by Formula IX is a halogen or a sulfonyloxy, wherein the halogen is selected from the group consisting of chlorine, bromine, or iodine; the sulfonyloxy is selected from the group consisting of benzenesulfonyloxy, p-toluenesulfonyloxy or methanesulfonyloxy; the base used is selected from the group consisting of potassium carbonate, sodium carbonate, sodium hydroxide or potassium hydroxide, preferably potassium carbonate; the molar ratio of the compound shown by Formula VIII to the compound shown by Formula IX is 1:1 to 1:3, preferably 1:1.4 to 1:2; the molar ratio of the compound shown by Formula VIII to the base is 1:1.5 to 1:4, preferably 1:2 to 1:3.5; the reaction solvent used is selected from the group consisting of methanol, ethanol, acetonitrile, water or a mixed solvent thereof, preferably a mixed solvent of ethanol and water; the reaction is performed under the temperature of 55 to 65° C.

In step (8), the reaction solvent used is selected from the group consisting of methanol, ethanol or isopropanol, preferably ethanol; the molar ratio of the compound shown by Formula XI to the phosphoric acid is 1:0.95 to 1:1.05; the reaction temperature is controlled to be 20 to 80° C., preferably 60 to 70° C.

The terms partly used in the present application are defined as follows:

"Halogen" refers to fluorine, chlorine, bromine, and iodine.

"Alkyl", as a group or part of a group, refers to a linear or branched aliphatic hydrocarbon group. $C_1$-$C_6$ alkyls are most preferred unless otherwise specified. Examples of linear or branched $C_1$-$C_6$ alkyl groups include but are not limited to methyl, ethyl, n-propyl, 2-propyl, n-butyl, isobutyl, tert-butyl, hexyl, and the like.

The preferred reaction conditions of the present application are listed in the following schemes:

Step (1):

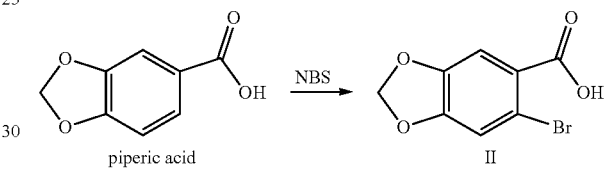

Step (2):

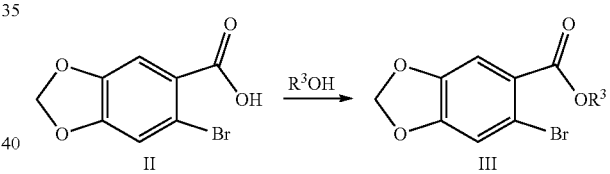

Step (3):

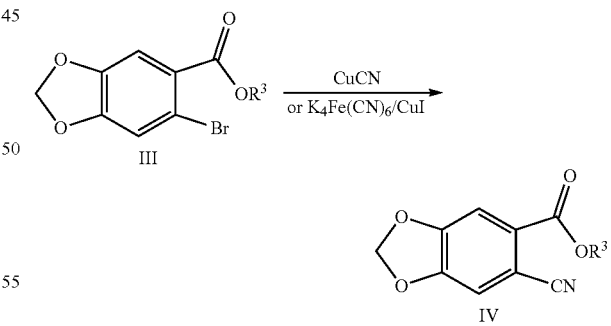

Step (4):

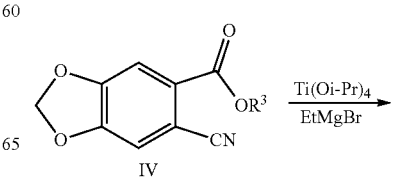

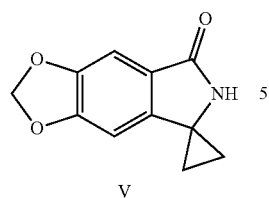

V

Step (5):

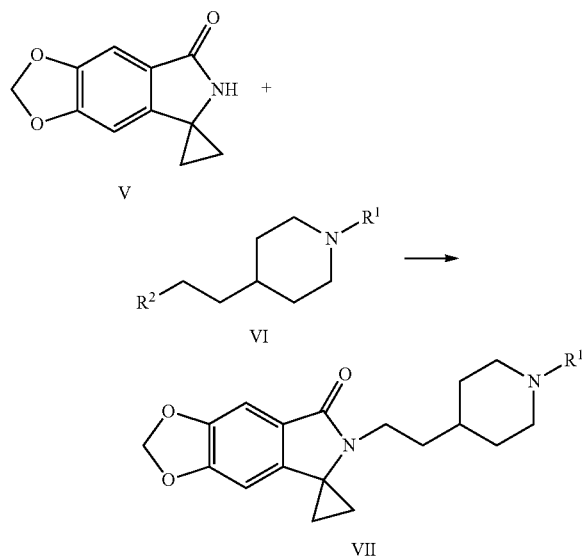

V

VI

VII

Step (6):

VII

VIII

Step (7):

VIII

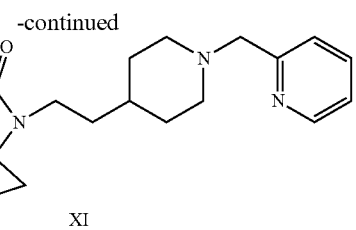

XI

Step (8):

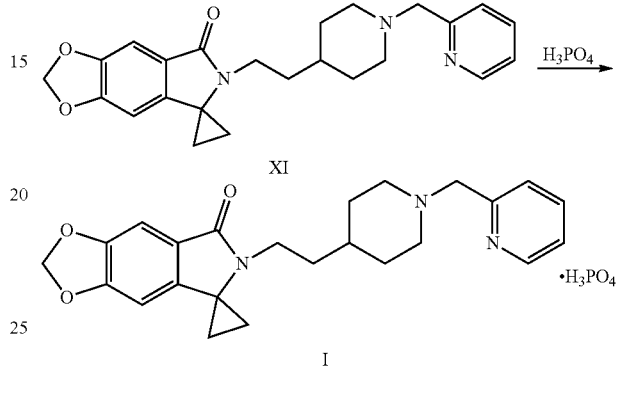

XI

I

DETAILED DESCRIPTION OF THE INVENTION

Hereinafter, the preparation method of the present application will be further described in detail with reference to the above reaction steps (1)-(8).

In step (1), the piperic acid is ortho-brominated under the action of N-bromosuccinimide (NBS) to form the compound shown by Formula II. It is well known to those skilled in the art that a bromination reaction usually takes place in an organic solvent (such as tetrahydrofuran, dichloromethane, chloroform, N,N-dimethylformamide). However, in the present application, it is preferable to select an inorganic solvent (preferably water) as the reaction solvent. Meanwhile, in order to increase the solubility of the raw material of piperic acid in water and to accelerate the reaction progress, an appropriate base is added to the reaction system to salify the carboxylic acid of the piperic acid, and thus the water solubility thereof is enhanced. Piperic acid (1 equivalent) and 1.2 to 2 equivalents of base (e.g., sodium hydroxide, potassium hydroxide, sodium bicarbonate, sodium carbonate, and potassium carbonate) are dissolved in water, and 1.4 to 2.4 equivalents of N-bromosuccinimide (NBS) is added thereto. Then reacting under the temperature of 0 to 70° C., preferably 30 to 45° C., until the reaction is completed, and followed by acidification with an acid (e.g., hydrochloric acid) so that the salified carboxyl is free and a solid is precipitated out and filtered to obtain a compound shown by Formula II; or the reaction is completed and followed by an acidification with an acid (such as hydrochloric acid), then extracted with an organic solvent (such as ethyl acetate), concentrated, and purified by pulping to obtain a compound shown by Formula II.

In the step (2), an esterification reaction is performed to the compound shown by Formula II with an alcohol ($R^3OH$) under the catalysis of an acid to obtain an ester shown by Formula III, and the acid used for catalysis is preferably concentrated sulfuric acid. The method is known in the art, see J. Am. Chem. Soc., 1997, 119 (18), 4097-4102.

In step (3), the compound shown by Formula III is cyanated under the action of a cyanide ion donor to obtain the cyano ester shown by Formula IV. The compound shown by Formula III (1 equivalent) is dissolved in an appropriate anhydrous solvent (for instance, N,N-dimethylformamide or N,N-dimethylacetamide) and the cyanide ion donor (preferably potassium ferrocyanide/cuprous iodide ($K_4Fe(CN)_6$/CuI) is added, in which the cuprous iodide (CuI) is fed in an amount of 1 to 2 equivalents (preferably 1.1 to 1.5 equivalents), the potassium ferrocyanide ($K_4Fe(CN)_6$) is dried under the temperature of 80° C. in advance, and is fed in an amount of 0.15 to 0.35 equivalent (preferably 0.18 to 0.25 equivalent). Then reaction is conducted under the temperature of 100 to 160° C., preferably 120 to 140° C. After the reaction is completed, a solid is precipitated out, separated and purified by methods of filtration, dissolution, decolorization and crystallization to obtain the compound shown by Formula IV.

In Step (4), a spiropropane lactam shown by Formula V is obtained from the cyano ester shown by Formula IV under the action of titanium (IV) isopropoxide ($Ti(Oi-Pr)_4$) and a Grignard reagent of ethylmagnesium halide. The cyano ester shown by Formula IV (1 equivalent) is dissolved in an anhydrous solvent (preferably dichloromethane), and 1 to 3 equivalents (preferably 1 to 1.5 equivalents) of titanium (IV) isopropoxide ($Ti(Oi-Pr)_4$) is added under the protection in a dry inert gas stream (for instance, nitrogen), 1 to 5 equivalents (preferably 2 to 3 equivalents) of Grignard reagent (preferably ethylmagnesium bromide) is slowly added dropwise to under the temperature of 0 to 35° C., preferably 0 to 20° C. Cyclopropanation and lactamization reactions are conducted successively, and then separated and purified by methods of decolorization and crystallization to obtain spiropropane lactam shown by Formula V.

In step (5), the spirocyclopropane lactam shown by Formula V is coupled with the compound shown by Formula VI under the action of a base to obtain a compound shown by Formula VII. The spirocyclopropane lactam shown by Formula V (1 equivalent) is dissolved in an organic solvent (preferably dimethyl sulfoxide), 1 to 3 equivalents (preferably 1.1 to 2 equivalents) of base (preferably sodium hydroxide or potassium hydroxide) and 1 to 3 equivalents (preferably 1.1 to 1.5 equivalents) of the compound shown by Formula VI are added. Then reaction is conducted for 3 to 4 hours under the temperature of 25 to 75° C., preferably 55 to 65° C. The compound shown by Formula VII is then obtained by extraction, separation and decolorization and used directly in the next step without further separation and purification.

In step (6), the protecting group of amino of the compound shown by Formula VII is removed. The protecting group of amino $R^1$ is tert-butyloxycarbonyl (Boc), and the compound shown by Formula VII is dissolved in an appropriate solvent (e.g. methanol, ethanol, ethyl acetate or a mixed solvent thereof, preferably a mixed solvent of ethanol and ethyl acetate, more preferably, the volume ratio of ethanol to ethyl acetate is 2:3) and the deprotection is performed under an acidic condition (such as sulfuric acid, trifluoroacetic acid, hydrofluoric acid, or hydrochloric acid, preferably hydrochloric acid) under the temperature of 20 to 70° C., preferably 50 to 60° C. After the reaction is completed, a solid is precipitated out after cooling, and then is filtered to obtain the compound shown by Formula VIII or a salt thereof.

The hydrochloric acid used in this reaction is not particularly limited, and any one of concentrated hydrochloric acid, hydrogen chloride gas, hydrogen chloride gas-absorbed solvent, solvent-diluted mixed liquid of concentrated hydrochloric acid may be used.

In step (7), a compound shown by Formula VIII or a salt thereof and a compound of Formula IX or a salt thereof are reacted under a basic condition to obtain a compound shown by Formula XI. 1 equivalent of the compound shown by Formula VIII or a salt thereof and 1 to 3 equivalents (preferably 1.4 to 2 equivalents) of the compound shown by Formula IX or a salt thereof (preferably 2-chloromethylpyridine hydrochloride) are dissolved in an appropriate solvent (e.g., methanol, ethanol, acetonitrile, water, or a mixed solvent thereof, preferably a mixed solvent of ethanol and water), then 1.5 to 4 equivalents (preferably 2 to 3.5 equivalents) of base (e.g., potassium carbonate, sodium carbonate, sodium hydroxide or potassium hydroxide, preferably potassium carbonate) is added. Then the reaction is conducted under the temperature of 55 to 65° C. After the reaction is completed, a solid is precipitated out after cooling, then separated and purified by methods of dissolution, decolorization and crystallization to obtain the compound shown by Formula XI.

In step (8), the compound shown by Formula XI is salified with phosphoric acid to obtain a compound of Formula I. The compound shown by Formula XI (1 equivalent) is dissolved in an appropriate solvent (e.g., methanol, ethanol or isopropanol, preferably ethanol) and 0.95 to 1.05 equivalents of phosphoric acid is added, then reacted under the temperature of 20 to 80° C., preferably 60° C. to 70° C. After the reaction is completed, a solid is precipitated out and filtered to obtain the compound of Formula I.

The piperic acid is used as a raw material in the present application and the compound of Formula (I) is obtained through bromination, esterification, cyanation, cyclopropane lactamization, alkylation of nitrogen in amide, deprotection, alkylation of nitrogen in piperidine and salification. Compared with the preparation method disclosed in WO2014005421, the advantages of the present application are summarized as follows:

a) The synthesis steps are reduced; a cinnamic acid is used as the raw material by the former process, and the compound of Formula (I) is prepared through a reaction of 10 steps; the piperic acid is used as the raw material by the process of the present application to prepare the compound of Formula (I) through a reaction of 8 steps; and the multi-steps reaction of the present application adopts a method of crystallization to separate and purify, which replaces the former column chromatography separation, thereby simplifying the purification operation and reduces the costs.

b) The present process is environmentally friendly; the toxic gases (nitrogen oxides) produced in the former process will not be produced in the production procedure, and heavy metals, highly toxic chemicals and dangerous reagents in the former process (such as vanadium pentoxide, stannic chloride, diethylzinc, phosphorus pentachloride, etc.) are not used, thereby improving production safety and operability.

c) The starting material (cinnamic acid) used in the former process is expensive and difficult to procure; the starting material (piperic acid) used in the present process is cheap and readily available.

d) The method of the present application is appropriate to industrial large-scale production with high yield.

In summary, through providing a process for producing a benzodioxole derivative and intermediates thereof, the clinical trial drug AD-35 for treating Alzheimer's disease is obtained in the present application using a cheap and readily available starting material with short synthesis route, simple operation, high yield, low cost, which is also appropriate to industrial production.

EXAMPLES

The following examples are only intended to further illustrate the present application and do not aim to any limitation to the present application.

Reference Example 1

Preparation of Raw Material tert-butyl 4-[2-(p-toluenesulfonyloxy)ethyl]piperidine-1-carboxylate (Formula VIa)

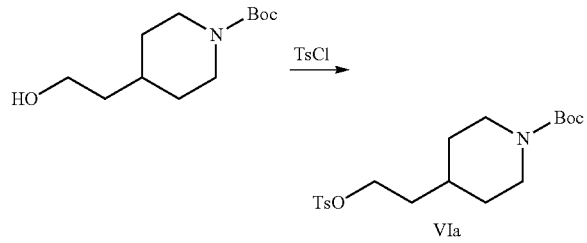

Into a 10 reaction flask, 800 g (3.49 mol) of tert-butyl 4-(2-hydroxyethyl)piperidine-1-carboxylate, 5 of dichloromethane, 974 ml (6.75 mol) of triethylamine and 16 g of 4-dimethylaminopyridine were added, the stirrer was turned on, 738 g (3.87 mol) of p-toluenesulfonyl chloride was added, the reaction was kept at 25 to 38° C. for 1.5 hours, the completion of the reaction was detected by TLC. Washed by adding water (3 L×3), the organic phase was collected, and dried over anhydrous sodium sulfate, filtered, and the filtrate was concentrated under reduced pressure to dryness to obtain 1360.3 g of compound VIa (HPLC purity: 85%). $^1$H NMR (DMSO-d$_6$): δ 0.85-0.93 (m, 2 H), 1.38 (s, 9 H), 1.42-1.52 (m, 5 H), 2.43 (s, 3 H), 2.59 (br s, 2 H), 3.84 (d, 2 H, J=11.3 Hz), 4.05 (t, 2 H, J=6.1 Hz), 7.50 (d, 2 H, J=8.1 Hz), 7.79 (d, 2 H, J=8.3 Hz); MS (ESI): m/z 383 [M+Na]$^+$.

Reference Example 2

Preparation of Raw Material tert-butyl 4-(2-iodoethyl)piperidine-1-carboxylate (Formula VIb)

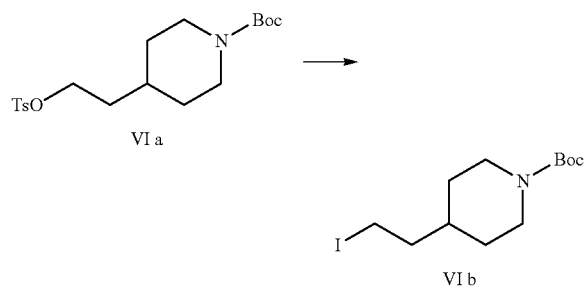

Into a 50 mL reaction flask, 5 g (13.0 mmol) of tert-butyl 4-[2-(p-toluenesulfonyloxy)ethyl]piperidine-1-carboxylate (Formula VIa), 35 mL of acetone, and 2.9 g (19.3 mmol) of sodium iodide were added, heated to reflux for 1 h, the completion of the reaction was detected by TLC. The acetone was removed by concentration, 50 mL of water and 50 mL of ethyl acetate were added for extracting, the organic phase was washed with 50 mL of water and collected, then the aqueous phase was extracted again with 50 mL of ethyl acetate, the aqueous phases were combined, dried over anhydrous sodium sulfate, filtered, and the filtrate was concentrated to dryness to obtain 3.5 g of compound VIb, yield: 79.5%. $^1$H NMR (DMSO-d$_6$): δ 0.97-1.07 (m, 2 H), 1.41 (s, 9 H), 1.51-1.58 (m, 1 H), 1.63-1.66 (m, 2 H), 1.73-1.78 (m, 2 H), 2.69 (br s, 2 H), 3.31 (t, 2 H, J=7.3 Hz), 3.96 (d, 2 H, J=10.3 Hz); MS (ESI): m/z 240 [M-Boc+H]$^+$.

Example 1

Preparation of 6-bromo-1,3-benzodioxole-5-carboxylic Acid (Compound II)

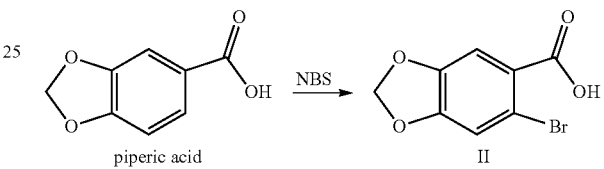

Into a 2 reaction flask, 100 g (0.60 mol) of piperic acid, 29 g (0.725 mol) of sodium hydroxide and 1 of water were successively added, and dissolved by stirring, 150 g (0.84 mol) of N-bromosuccinimide was added, the reaction was kept at 30 to 45° C. for 45 min, the completion of the reaction was detected by TLC. Concentrated hydrochloric acid was added dropwise to adjust the pH of the reaction solution to 2 to 3, a solid was precipitated out, cooled with ice water, filtrated, the filter cake was washed with water, dried to obtain 117.4 g of compound II (HPLC purity: 82%), yield: 79.5%. $^1$H NMR (DMSO-d$_6$): δ 6.15 (s, 2 H), 7.30 (s, 1 H), 7.32 (s, 1 H), 13.17 (s, 1 H).

Example 2

Preparation of 6-bromo-1,3-benzodioxole-5-carboxylic Acid (Compound II)

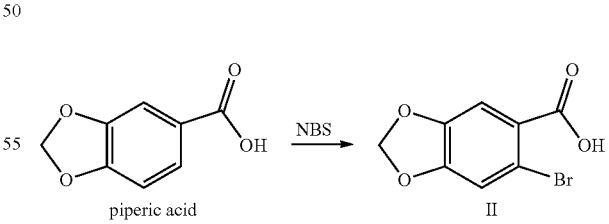

Into a 2 reaction flask, 100 g (0.60 mol) of piperic acid, 29 g (0.725 mol) of sodium hydroxide and 1 of water were successively added, dissolved by stirring, 150 g (0.84 mol) of N-bromosuccinimide was added, the reaction was kept at 30 to 45° C. for 45 min, the completion of the reaction was monitored by TLC. 1 of ethyl acetate and 40 mL of concentrated hydrochloric acid were added, stirred for 20 min, layered, the organic phase was collected, concentrated to dryness, 200 mL of water and 600 mL petroleum ether were further added, stirred for 1 h, filtered, the filter cake was washed with water, dried to obtain 116 g of compound II (HPLC purity: 92.0%), yield: 78.9%. The ¹H NMR data is the same as in those of Example 1.

Example 3

Preparation of ethyl 6-bromo-1,3-benzodioxole-5-carboxylate (Compound IIIa)

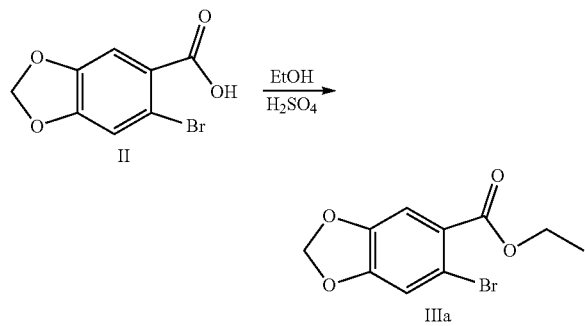

Into a 2 reaction flask, 117.3 g (0.39 mol) of 6-bromo-1,3-benzodioxole-5-carboxylic acid (II), 585 mL of anhydrous ethanol were added, the stirrer was turned on, 77 mL (1.4 mol) of concentrated sulfuric acid was added slowly, it was heated to reflux and the reaction was kept for 6 h, the completion of the reaction was monitored by TLC. Cooled with ice water, 1.2 of water was added dropwise, a solid was precipitated out, filtrated, the filter cake was washed with water, dried at 35-45° C. to obtain 124.0 g of compound IIIa (HPLC purity: 85%), yield: 93.9%. ¹H NMR (CDCl₃): δ 1.39 (t, 3 H, J=7.1 Hz), 4.34 (q, 2 H, J=7.1 Hz), 6.04 (s, 2 H), 7.07 (s, 1 H), 7.31 (s, 1 H).

Example 4

Preparation of methyl 6-bromo-1,3-benzodioxole-5-carboxylate (Compound IIIb)

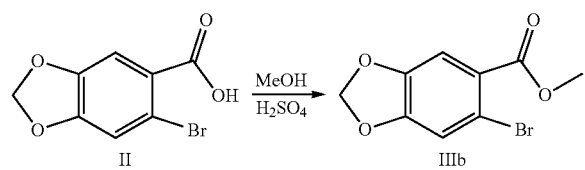

Into a 1 reaction flask, 50 g (0.30 mol) of 6-bromo-1,3-benzodioxole-5-carboxylic acid (II) and 500 mL of anhydrous methanol were added, and the stirrer was turned on, 33.3 mL (0.60 mol) of concentrated sulfuric acid was added dropwise under the cooling of ice water and the mixture was heated to reflux for 6 h, the completion of the reaction was monitored by TLC. Cooled with ice water, a solid was precipitated out, 500 mL of water was added dropwise, filtrated, the filter cake was washed with water, dried at 45 to 55° C. to obtain 44.4 g of compound IIIb, yield: 84.0%. ¹H NMR (DMSO-d₆): δ 3.83 (s, 3 H), 6.19 (s, 2 H), 7.35 (s, 1 H), 7.36 (s, 1 H).

Example 5

Preparation of ethyl 6-cyano-1,3-benzodioxole-5-carboxylate (Compound IVa)

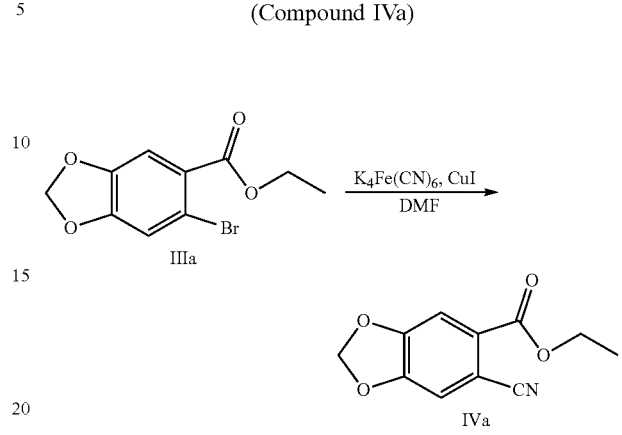

Into a 2 reaction flask, 124 g (0.38 mol) of ethyl 6-bromo-1,3-benzodioxole-5-carboxylate (IIIa), 990 mL of N,N-dimethylformamide were added, and the stirrer was turned on, 33.1 g (0.09 mol) potassium ferrocyanide and 103.3 g (0.54 mol) cuprous iodide were added, and heated to 120 to 140° C., the reaction was kept for 5 h, the completion of the reaction was monitored by TLC. Cooled, water was added to precipitate the solid out, filtered, and the filter cake was washed with water. The filter cake was stirred in 1.9 of dichloromethane for 30 min, filtered, and 9 g of activated carbon was added to the filtrate, decolored for 30 min, filtered, and the filtrate was concentrated to a small amount, a solid was precipitated out, n-hexane was added dropwise, cooled with ice water, filtered, and dried to obtain 82.8 g of Compound IVa (HPLC purity: 99.5%), yield: 83.2%. ¹H NMR (DMSO-d₆): δ 1.34 (t, 3 H, J=7.1 Hz), 4.33 (q, 2 H, J=7.1 Hz), 6.29 (s, 2 H), 7.51 (s, 1 H), 7.57 (s, 1 H).

Example 6

Preparation of ethyl 6-cyano-1,3-benzodioxol-5-carboxylate (Compound IVa)

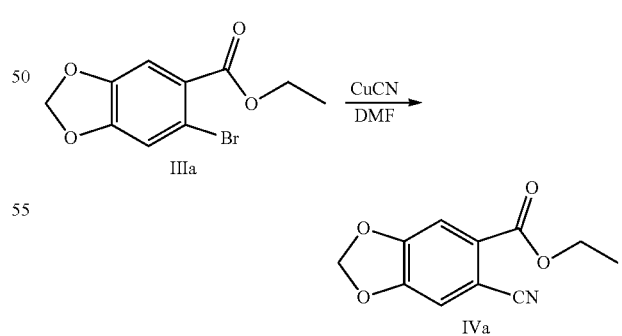

Into a 50 mL reaction flask, 3.5 g (12.8 mmol) of ethyl 6-bromo-1,3-benzodioxole-5-carboxylate (IIIa), 35 mL of N,N-dimethylformamide, 2.3 g (25.7 mmol) of cuprous cyanide were added, stirring was started, the reaction was kept at 120 to 140° C. for 30-60 min, the completion of the reaction was monitored by TLC. Cooled, 30 mL saturated aqueous ammonium chloride solution was added dropwise, a solid was precipitated out, filtered, and the filter cake was washed with water. The filter cake was dissolved in 200 mL of ethyl acetate and washed with saturated aqueous ammonium chloride solution (30 mL×2 times), the organic phase was collected, and the aqueous phase was extracted once more with 100 mL of ethyl acetate, the organic phase was combined, dried over anhydrous sodium sulfate, filtered, concentrated, and crystallized to obtain 2.0 g of compound IVa, yield: 62.5%. The $^1$H NMR data is the same as in Example 5.

Example 7

Preparation of methyl 6-cyano-1,3-benzodioxole-5-carboxylate (Compound IVb)

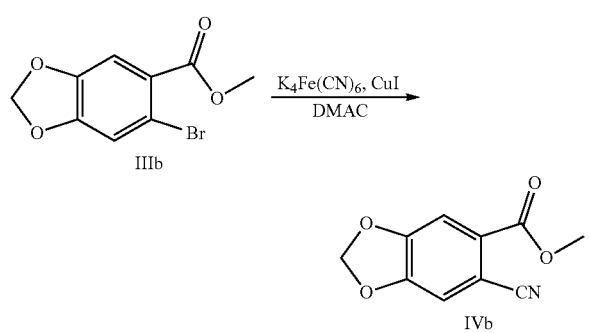

Into a 1 reaction flask, 40 g (0.15 mol) of methyl 6-bromo-1,3-benzodioxole-5-carboxylate (IIIb), 11.4 g (31.0 mmol) of potassium ferrocyanide, 35.2 g (0.18 mol) of cuprous iodide, 240 mL of N,N-dimethylacetamide were added, the reaction was kept at an oil bath heating of 120 to 140° C. for 2 to 3 h, the completion of the reaction was monitored by TLC. Cooled, 480 mL of water was added dropwise, the solid was precipitated out, cooled with ice water, filtered, and the filter cake was washed with water. The filter cake was dissolved in a mixed liquor of 500 mL of ethyl acetate and 200 mL of tetrahydrofuran, heated to 80° C., 2 g of activated carbon was added, filtered, and the filtrate was concentrated to a small amount, a solid was precipitated out, 200 mL of petroleum ether was added dropwise, cooled with ice water, filtered, the filter cake was washed with petroleum ether and dried to obtain 27.7 g of compound IVb, yield: 87.6%. $^1$H NMR (DMSO-d$_6$): δ 3.87 (s, 3 H), 6.28 (s, 2 H), 7.49 (s, 1 H), 7.55 (s, 1 H).

Example 8

Preparation of spiro[6H-[1,3]dioxolo[4,5-f]isoindole-7,1'-cyclopropane]-5-one (Compound V)

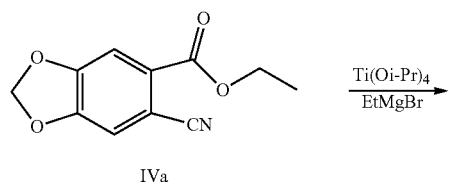

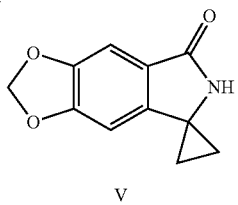

Into a 2 reaction flask, 16 g (0.072 mol) of compound of Formula IVa and 160 mL of methylene chloride were added, dissolved by stirring, and protected with nitrogen, 24 mL (0.080 mol) of titanium (IV) isopropoxide was added, cooled to 0 to 20° C., 73 mL (0.22 mol) of solution of ethylmagnesium bromide in diethyl ether (3 M) was slowly added dropwise, the completion of the reaction was monitored by TLC after the addition was completed. Water/tetrahydrofuran solution (64 mL water/240 mL tetrahydrofuran) was added dropwise slowly, heated to 50° C., 2 g of activated charcoal was added to decolorize, and stirred for 20 min, filtered, and the residue was washed with ethyl acetate, the filtrate was concentrated at 40 to 50° C. under reduced pressure to dryness, 96 mL of ethyl acetate and 96 mL of water were added, a solid was precipitated out by stirring, 290 mL of hexane was added dropwise, cooled with ice water, filtered, the filter cake was washed with n-hexane and dried to obtain 11.9 g of compound V (HPLC purity: 70%), yield: 80.2%. $^1$H NMR (DMSO-d$_6$): δ 1.33-1.41 (m, 4 H), 6.11 (s, 2 H), 6.86 (s, 1 H), 7.09 (s, 1 H), 8.53 (s, 1 H).

Example 9

Preparation of spiro[6H-[1,3]dioxolo[4,5-f]isoindole-7,1'-cyclopropane]-5-one (Compound V)

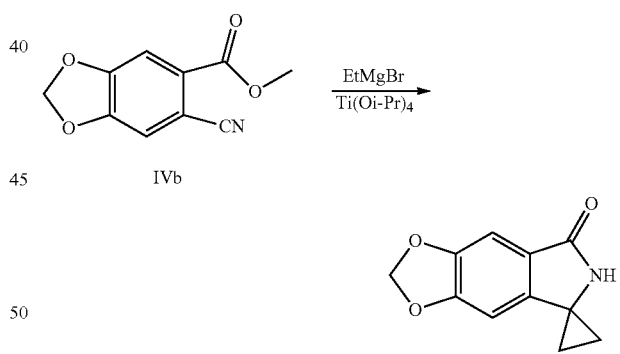

Into a 500 mL reaction flask, 10 g (48.8 mmol) of methyl 6-cyano-1,3-benzodioxole-5-carboxylate (IVb), 200 mL of methyl tert-butyl ether, 15 mL (50.7 mmol) of titanium (IV) isopropoxide were added, cooled to 0 to 20° C., 49 mL (0.15 mol) of solution of ethylmagnesium bromide in diethyl ether (3 M) was added dropwise slowly, the completion of the reaction was monitored by TLC after the addition was completed. 20 mL of hydrochloric acid was added dropwise, followed by extraction with 250 mL of ethyl acetate, the organic phase was washed with water (100 mL×2 times) and collected, the aqueous phase was extracted once more with 100 mL of ethyl acetate, the organic phase was combined, dried with anhydrous sodium sulfate, decolorized with activated carbon, filtered, the filtrate was concentrated to a small amount, petroleum ether was added dropwise, cooled with ice water, filtered, the filter cake was washed with petroleum ether, and dried to obtain 2.3 g of compound V, yield: 23.2%. The ¹H NMR data is the same as in Example 8.

Example 10

Preparation of tert-butyl 4-[2-(5-oxospiro[[1,3]di-oxolo[4,5-f]isoindole-7,1'-cyclopropane]-6-yl) ethyl] piperidine-1-carboxylate (Compound VIIa)

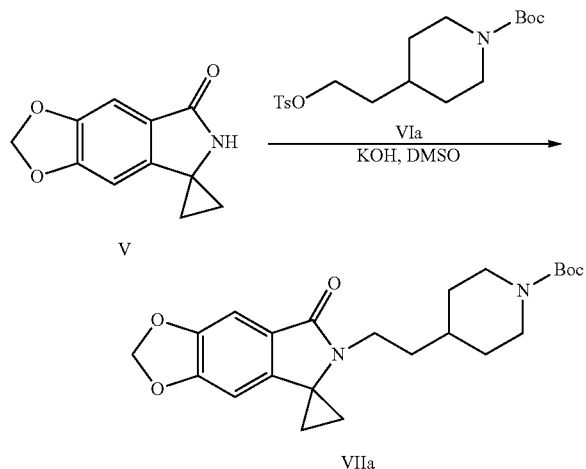

Into a 250 mL reaction flask, 11.9 g (0.041 mol) of compound V, 84 mL of dimethyl sulfoxide, 4 g (0.071 mol) of potassium hydroxide, 27.3 g (0.06 mol) of tert-butyl 4-[2-(p-toluenesulfonyloxy)ethyl]piperidine-1-carboxylate (Formula VIa) were added, heated to 55 to 65° C. for 3-4 hours, the completion of the reaction was monitored by TLC. Cooled, 150 mL of water was added, extracted with 300 mL ethyl acetate, the organic phase was collected and washed with water (150 mL×2 times), the aqueous phase was extracted once more with 200 mL ethyl acetate, the organic phase was combined and decolorized by adding 3 g of activated carbon, stirred for 30 min, filtered and the filtrate was concentrated to dryness under reduced pressure to obtain compound VIIa. ¹H NMR (CDCl₃): δ 1.08-1.19 (m, 2 H), 1.28 (dd, 2 H, J=6.2, 7.4 Hz), 1.45 (s, 9 H), 1.48-1.57 (m, 5 H), 1.72 (d, 2 H, J=12.7 Hz), 2.69 (t, 2 H, J=11.6 Hz), 3.20 (t, 2H, J=7.6 Hz), 4.07 (d, 2 H, J=13.1 Hz), 6.03 (s, 2H), 6.43 (s, 1H), 7.23 (s, 1H); MS (ESI): m/z 437 [M+Na]⁺.

Example 11

Preparation of tert-butyl 4-[2-(5-oxospiro[[1,3]di-oxolo[4,5-f]isoindole-7,1'-cyclopropane]-6-yl)ethyl] piperidine-1-carboxylate (Compound VIIa)

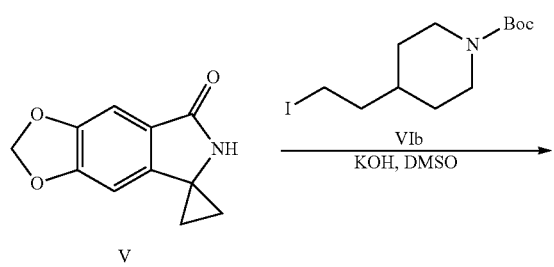

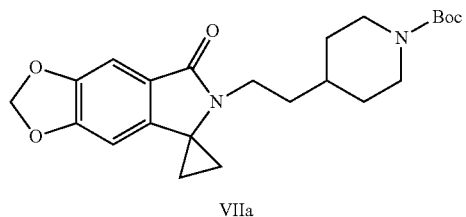

Into a 250 mL reaction flask, 6.7 g (33.0 mmol) of the compound of Formula V, 100 mL of N,N-dimethylformamide, 2.6 g (65.0 mmol) of sodium hydroxide, and 14 g (41.3 mmol) of tert-butyl 4-(2-iodoethyl)piperidine-1-carboxylate (VIb) were added, the reaction was kept at 25-30° C. for 1.5 h, the completion of the reaction was monitored by TLC. 100 mL of water and 100 mL of ethyl acetate were added, extracted, and the organic phase was washed with water (50 mL×2 times), the organic phase was collected, and the aqueous phase was extracted once more with 100 mL of ethyl acetate, the organic phase was combined, dried over anhydrous sodium sulfate, filtered, and the filtrate was concentrated to dryness to obtain compound VIIa. The ¹H NMR data is the same as those in Example 10.

Example 12

Preparation of 6-[2-(4-piperidine)ethyl]spiro[[1,3] dioxolo[4,5-f]isoindole-7,1'-cyclopropane]-5-one hydrochloride (Compound VIIIa)

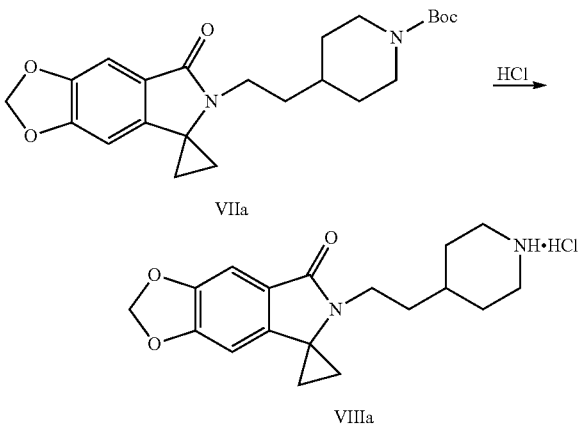

Into a 100 mL reaction flask, the compound of Formula VIIa obtained in Example 10, 30 mL of ethanol, 45 mL of ethyl acetate, and 10.5 mL of concentrated hydrochloric acid were added, the stirrer was turned on, and the reaction was kept at 50-60° C. for 3 hours, the completion of the reaction was monitored by TLC, the heating was stopped. Cooled with ice water, filtered, and the filter cake was washed with ethyl acetate and dried to obtain 8.5 g of an off-white solid (compound VIIIa, HPLC purity: 97%), yield: 41.4% (calculated based on the feeding amount of compound V in Example 10). ¹H NMR (D₂O): δ 1.06 (t, 2 H, J=6.7 Hz), 1.32-1.46 (m, 6 H), 1.60 (m, 1 H), 1.91 (d, 2 H, J=13.5 Hz), 2.91-3.03 (m, 4 H), 3.39 (d, 2 H, J=12.8 Hz), 5.90 (s, 2 H), 6.18 (s, 1 H), 6.68 (s, 1 H); MS (ESI): m/z 315 [M−Cl]⁺.

Example 13

Preparation of 6-[2-[1-(2-pyridylmethyl)-4-piperidinyl]ethyl]spiro[[1,3]dioxolo[4,5-f]isoindole-7,1'-cyclopropane]-5-one (Compound XI)

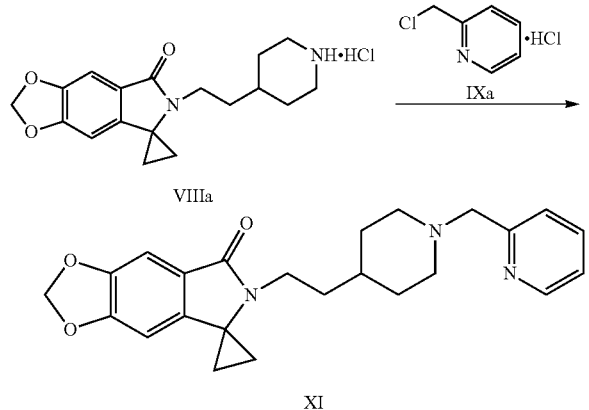

Into a 2 reaction flask, 128.6 g (0.35 mol) of the compound of Formula VIIIa, 90 g (0.54 mol) of 2-chloromethyl pyridine hydrochloride (Formula IXa), 965 mL of water, and 26 g of activated charcoal were added, decolorized at 60 to 65° C. for 30 min, filtered, the filter residue was washed with 643 ml of water and 215 mL of ethanol, 161 g (1.16 mol) of potassium carbonate was slowly added into the filtrate, the reaction was kept at 55 to 65° C. for 4-5 hours, the completion of the reaction was monitored by TLC. Cooled with ice water, filtered, dried to obtain 137 g of crude product; the crude product was dissolved in 1.37 of ethanol, dissolved by heating to 60 to 65° C., and decolorized with activated carbon (27.4 g/time×2 times), 4.11 of water was added dropwise to the filtrate, a solid was precipitated out, cooled with ice water, filtered, the filter cake was washed with water and dried to obtain 118.9 g of compound XI, yield: 80.0%. $^1$H NMR (CDCl$_3$): δ 1.26 (dd, 2 H, J=6.1, 7.6 Hz), 1.35 (br s, 3 H), 1.49-1.57 (m, 4 H), 1.72 (d, 2 H, J=8.6 Hz), 2.08 (t, 2 H, J=10.4 Hz), 2.89 (d, 2 H, J=10.7 Hz), 3.19 (t, 2 H, J=7.9 Hz), 3.64 (s, 2 H), 6.03 (s, 2 H), 6.42 (s, 1 H), 7.15 (dd, 1 H, J=5.2, 6.7 Hz), 7.24 (s, 1 H), 7.41 (d, 1 H, J=7.7 Hz), 7.64 (td, 1 H, J=7.6, 1.8 Hz), 8.55 (d, 1 H, J=4.2 Hz); MS (ESI): m/z 406 [M+H]$^+$.

Example 14

Preparation of 6-[2-[1-(2-pyridylmethyl)-4-piperidinyl]ethyl]spiro[[1,3]dioxolo[4,5-f]isoindole-7,1'-cyclopropane]-5-one phosphate (Compound I)

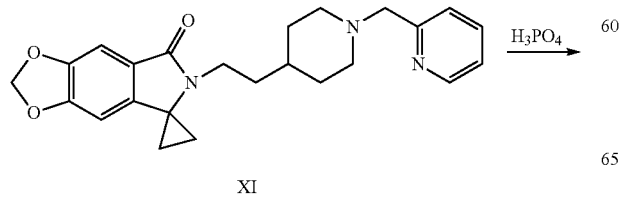

Into a 50 mL reaction flask, 2 g (4.9 mmol) of the compound of the Formula XI and 40 mL of ethanol were added, dissolved by heating at 60 to 70° C., and 0.57 g of 85% (4.9 mmol) phosphoric acid was added under stirring, a solid was precipitated out, 40 mL of ethyl acetate was added dropwise, cooled to room temperature, stirred for 1 hour, filtered, the filter cake was washed with a small amount of ethyl acetate, dried to obtain 2.3 g of a white solid (Compound I, HPLC purity: 99.8%), yield: 92.7%. $^1$H NMR (D$_2$O): δ 1.10 (t, 2 H, J=7.2 Hz), 1.33-1.64 (m, 7 H), 1.92 (d, 2 H, J=13.4 Hz), 2.95-3.09 (m, 4 H), 3.46 (d, 2 H, J=10.7 Hz), 4.34 (s, 2 H), 5.89 (s, 2 H), 6.20 (s, 1 H), 6.69 (s, 1 H), 7.45 (dd, 1 H, J=5.2, 7.4 Hz), 7.53 (d, 1 H, J=7.8 Hz), 7.88 (td, 1 H, J=7.7, 1.2 Hz), 8.54 (d, 1 H, J=4.6 Hz).

The invention claimed is:
1. A compound of Formula V:

2. A method for preparing a compound represented by Formula V, the method comprises: performing a cyclopropane lactamization of a cyano ester shown by Formula IV under titanium (IV) isopropoxide (Ti(Oi-Pr)$_4$) and a Grignard reagent of ethylmagnesium halide to obtain a spirocyclopropane lactam shown by Formula V:

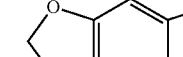

wherein R$^3$ is C$_1$-C$_6$ alkyl; X is chlorine, bromine or iodine.

3. The method of claim 2, characterized in that the Grignard reagent of ethylmagnesium halide is ethylmagnesium bromide.

4. The method of claim 2, characterized in that a reaction solvent is selected from the group consisting of diethyl ether, dichloromethane, toluene, methyl tert-butyl ether or tetrahydrofuran.

5. The method of claim 2, characterized in that a reaction temperature is controlled to be 0 to 35° C.

6. The method of claim 2, characterized in that a molar ratio of the compound shown by Formula IV to titanium (IV) isopropoxide (Ti(Oi-Pr)$_4$) is 1:1 to 1:3.

7. The method of claim 2, characterized in that a molar ratio of the compound shown by Formula IV to the Grignard reagent of ethylmagnesium halide is 1:1 to 1:5.

8. The method of claim 2, characterized in that the method for preparing the compound shown by Formula IV comprises:

Step 1: In solvent, salifying piperic acid under the action of a base and following with a bromination under the action of N-bromosuccinimide (NBS) to obtain a compound shown by Formula II:

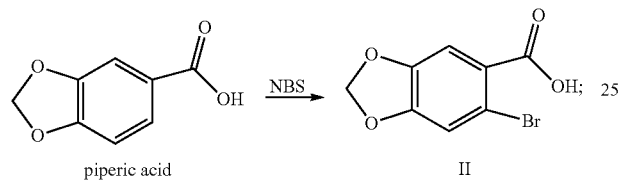

piperic acid   II

Step 2: Performing an esterification reaction of a compound shown by Formula II with an alcohol (R$^3$OH) under a catalysis of an acid to obtain an ester shown by Formula III:

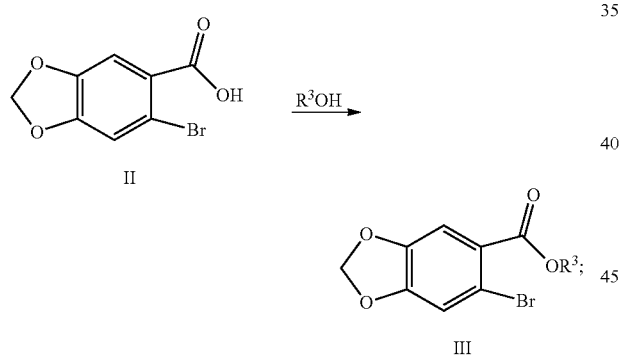

II

III

Step 3: Cyaniding a compound shown by Formula III under the action of a cyanide ion donor to obtain a cyano ester shown by Formula IV:

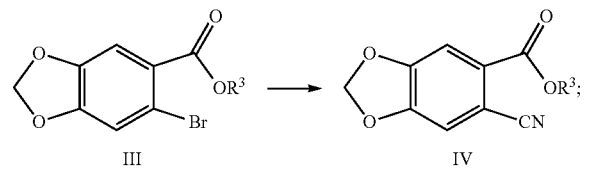

III   IV wherein R$^3$ is a C$_1$-C$_6$ alkyl.

9. The method of claim 8, wherein in Step 1, a reaction solvent is selected from the group consisting of N,N-dimethylformamide, N,N-dimethylacetamide, water, dichloromethane or chloroform; the base is selected from the group consisting of sodium hydroxide, potassium hydroxide, sodium hydrogencarbonate, sodium carbonate or potassium carbonate; a molar ratio of the piperic acid, base and N-bromosuccinimide (NBS) is 1:1.2-2:1.4-2.4; a reaction temperature is controlled to be 0 to 70° C.;

in Step 2, R$^3$ is methyl, ethyl or isopropyl; the acid is concentrated sulfuric acid;

in Step 3, the cyanide ion donor is selected from metal cyanide.

10. A method for preparing a compound represented by Formula VII from a compound represented by Formula V, the method comprises: coupling a spirocyclopropane lactam shown by Formula V with a compound shown by Formula VI under the action of a base to obtain a compound shown by Formula VII:

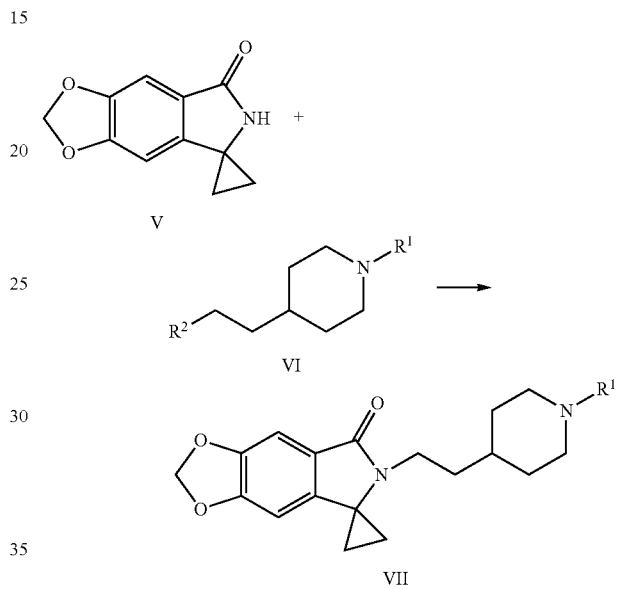

wherein R$^1$ is a protecting group of amino; R$^2$ is halogen or p-toluenesulfonyloxy.

11. The method of claim 10, characterized in that the base is selected from the group consisting of sodium hydride, potassium tert-butoxide, sodium hydroxide, potassium hydroxide or cesium carbonate.

12. The method of claim 10, characterized in that a molar ratio of the compound shown by Formula V to the base is 1:1 to 1:3.

13. The method of claim 10, characterized in that a molar ratio of the compound shown by Formula V to the compound shown by Formula VI is from 1:1 to 1:3.

14. The method of claim 10, characterized in that a reaction solvent is selected from the group consisting of N,N-dimethylformamide, dimethyl sulphoxide or acetonitrile.

15. The method of claim 10, characterized in that a reaction temperature is 25 to 75° C.

16. A method for preparing a compound represented by Formula (I),

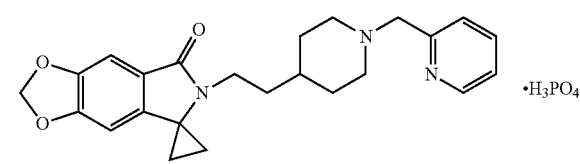

comprising the following steps:
(a) coupling a spirocyclopropane lactam shown by Formula V with a compound shown by Formula VI under the action of a base to obtain a compound shown by the Formula VII:

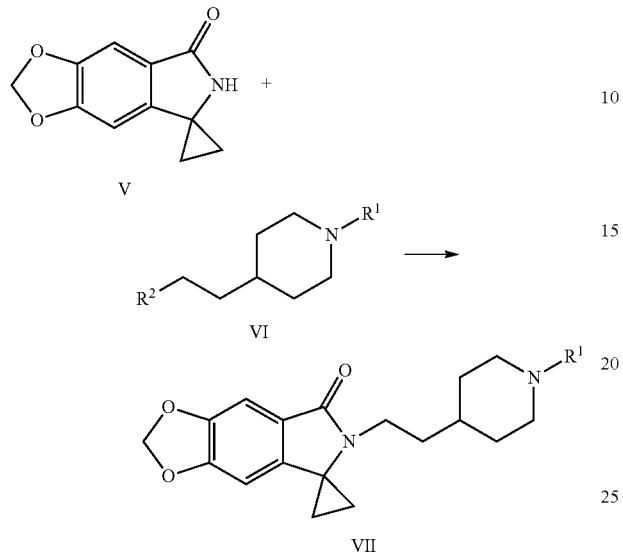

wherein $R^1$ is a protecting group of amino; $R^2$ is halogen or p-toluenesulfonyloxy;

(b) removing a protecting group of amino of the compound shown by Formula VII to obtain a compound shown by Formula VIII or a salt thereof:

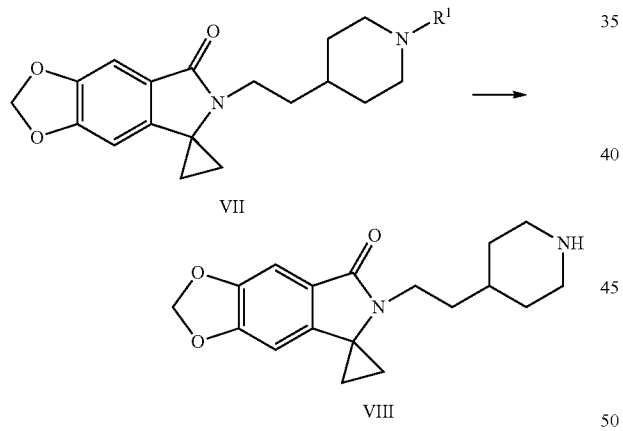

wherein $R^1$ is an protecting group of amino;

(c) reacting the compound shown by Formula VIII or a salt thereof with a compound shown by Formula IX or a salt thereof under the action of a base to obtain a compound shown by Formula XI:

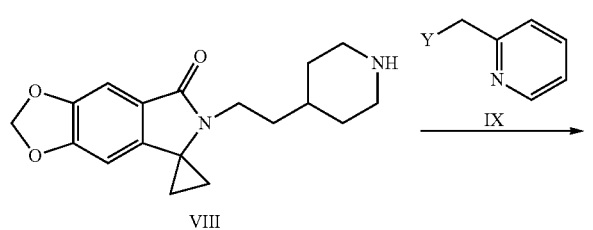

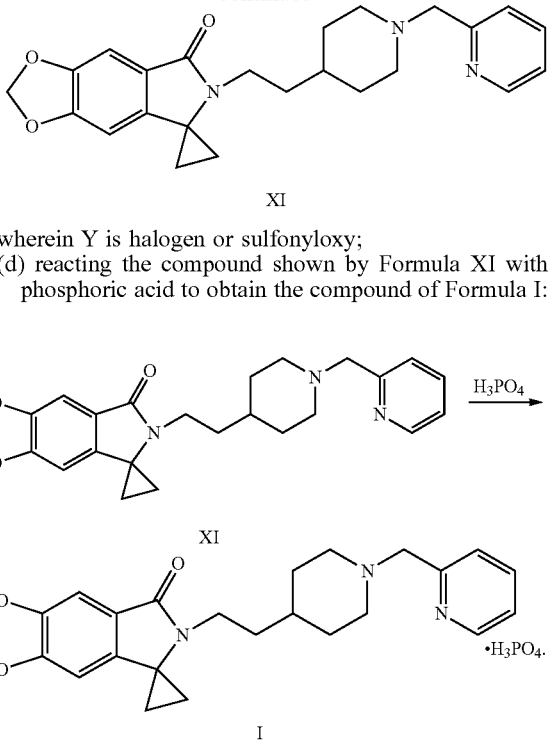

wherein Y is halogen or sulfonyloxy;
(d) reacting the compound shown by Formula XI with phosphoric acid to obtain the compound of Formula I:

17. The method of claim 16, wherein
in step (a), the base is selected from the group consisting of sodium hydride, potassium tert-butoxide, sodium hydroxide, potassium hydroxide or cesium carbonate; a molar ratio of the compound shown by Formula V to the base is 1:1 to 1:3; a molar ratio of the compound shown by Formula V to the compound shown by Formula VI is 1:1 to 1:3; a reaction solvent is selected from the group consisting of N,N-dimethylformamide, dimethyl sulfoxide or acetonitrile, a reaction temperature is 25 to 75° C.;

in step (b), when $R^1$ is tert-butoxycarbonyl, and when removing the protecting group of amino under an acidic condition, the acid is selected from the group consisting of sulfuric acid, trifluoroacetic acid, hydrofluoric acid or hydrochloric acid; a reaction solvent used is selected from the group consisting of methanol, ethanol, ethyl acetate or a mixed solvent thereof; a reaction temperature is controlled to be 20 to 70° C.;

in step (c), when Y in the compound shown by Formula IX is a halogen or a sulfonyloxy; the base is selected from the group consisting of potassium carbonate, sodium carbonate, sodium hydroxide or potassium hydroxide; a molar ratio of the compound shown by Formula VIII to the compound shown by Formula IX is 1:1 to 1:3; a molar ratio of the compound shown by Formula VIII to the base is 1:1.5 to 1:4; a reaction solvent used is selected from the group consisting of methanol, ethanol, acetonitrile, water or a mixed solvent thereof;

in step (d), a reaction solvent used is selected from the group consisting of methanol, ethanol or isopropanol; a molar ratio of the compound shown by Formula XI to phosphoric acid is 1:0.95 to 1.05; a reaction temperature is controlled to be 20 to 80° C.

18. The method of claim 16, characterized in that the compound shown by Formula V is prepared by the following method:

Step 1: in a solvent, salifying piperic acid under the action of a base and following with a bromination under the action of N-bromosuccinimide (NBS) to obtain a compound shown by Formula II:

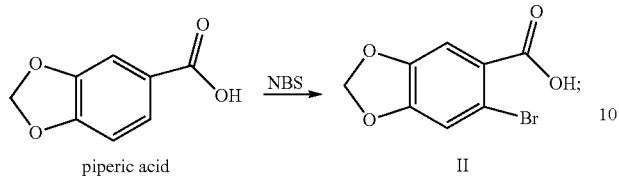

Step 2: performing an esterification reaction of the compound shown by Formula II with an alcohol ($R^3OH$) under a catalysis of an acid to obtain an ester shown by Formula III:

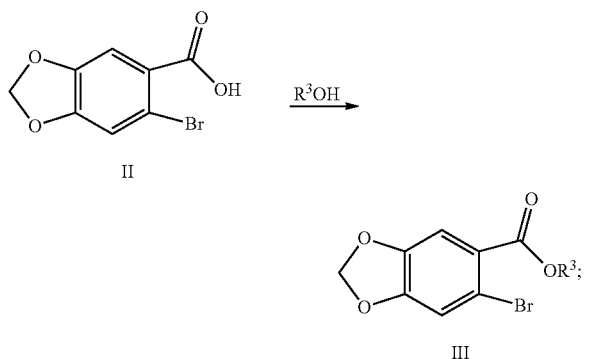

Step 3: cyaniding the compound shown by Formula III under the action of a cyanide ion donor to obtain a cyano ester shown by Formula IV:

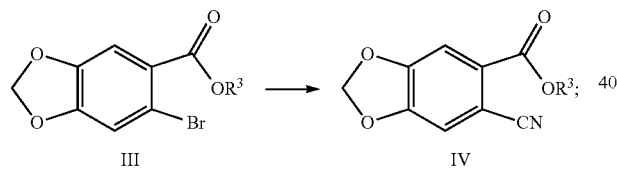

Step 4: performing a cyclopropane lactamization of a cyano ester shown by Formula IV under the action of titanium (IV) isopropoxide (Ti(Oi-Pr)$_4$) and a Grignard reagent of ethylmagnesium halide to obtain a spirocyclopropane lactam shown by Formula V:

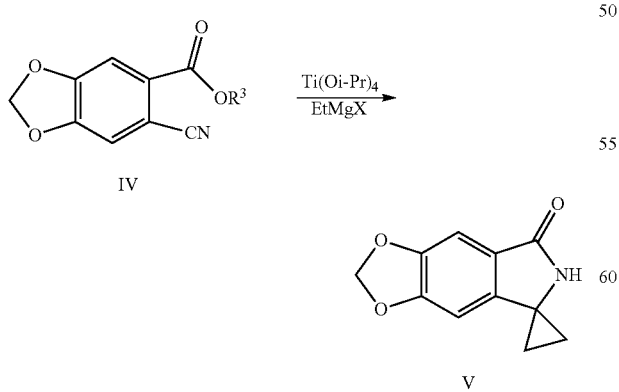

wherein $R^3$ is $C_1$-$C_6$ alkyl; X is chlorine, bromine or iodine.

19. The method of claim 9, wherein
in Step 1, a reaction solvent is water; a reaction temperature is controlled to be 30 to 45° C.;
in Step 2, $R^3$ is ethyl;
in Step 3, the cyanide ion donor is selected from cuprous cyanide (CuCN) or potassium ferrocyanide/copper iodide ($K_4Fe(CN)_6$/CuI).

20. The method of claim 9, wherein
in Step 3, the cyanide ion donor is potassium ferrocyanide/cuprous iodide ($K_4Fe(CN)_6$/CuI);
a molar ratio of the compound shown by Formula III to cuprous iodide (CuI) is 1:1 to 1:2, a molar ratio of the compound shown by Formula III to potassium ferrocyanide ($K_4Fe(CN)_6$) is 1:0.15 to 1:0.35, a reaction temperature is controlled to be 100 to 160° C.; the reaction solvent is selected from N,N-dimethylformamide or N,N-dimethylacetamide.

21. The method of claim 9, wherein
in Step 3, a molar ratio of the compound shown by Formula III to cuprous iodide (CuI) is 1:1.1 to 1:1.5; a molar ratio of the compound shown by Formula III to potassium ferrocyanide ($K_4Fe(CN)_6$) is 1:0.18 to 1:0.25, a reaction temperature is controlled to be 120 to 140° C.

22. The method of claim 10, wherein $R^1$ is tert-butoxycarbonyl (Boc).

23. The method of claim 11, wherein the base is selected from the group consisting of sodium hydroxide or potassium hydroxide.

24. The method of claim 16, wherein $R^1$ is tert-butoxycarbonyl (Boc).

25. The method of claim 17, wherein
in step (a), the base is selected from the group consisting of sodium hydroxide or potassium hydroxide; a molar ratio of the compound shown by Formula V to the base is 1:1.1 to 1:2; a molar ratio of the compound shown by Formula V to the compound shown by Formula VI is 1:1.1 to 1:1.5; a reaction solvent is dimethyl sulfoxide, a reaction temperature is 55 to 65° C.;
in step (b), when $R^1$ is tert-butoxycarbonyl, and when removing the protecting group of amino under an acidic condition, the acid is hydrochloric acid; a reaction solvent used is a mixed solvent of ethanol and ethyl acetate; a reaction temperature is controlled to be 50 to 60° C.;
in step (c), when Y in the compound shown by Formula IX is selected from the group consisting of chlorine, bromine, iodine, benzenesulfonyloxy, p-toluenesulfonyloxy or methanesulfonyloxy; the base is potassium carbonate; a molar ratio of the compound shown by Formula VIII to the compound shown by Formula IX is 1:1.4 to 1:2; a molar ratio of the compound shown by Formula VIII to the base is 1:2 to 1:3.5; a reaction solvent used is a mixed solvent of ethanol and water;
in step (d), a reaction solvent used is ethanol; a reaction temperature is controlled to be 60 to 70° C.

26. The method of claim 17, wherein
in step (b), a reaction solvent used is a mixed solvent of ethanol and ethyl acetate, wherein a volume ratio of ethanol to ethyl acetate is 2:3.

* * * * *